(12) United States Patent
Watanabe et al.

(10) Patent No.: US 9,739,412 B2
(45) Date of Patent: Aug. 22, 2017

(54) METHOD OF EXTENDING LIFE EXPECTANCY OF HIGH-TEMPERATURE PIPING AND LIFE EXPECTANCY EXTENSION STRUCTURE OF HIGH-TEMPERATURE PIPING

(71) Applicant: MITSUBISHI HITACHI POWER SYSTEMS, LTD., Kanagawa (JP)

(72) Inventors: Daigo Watanabe, Tokyo (JP); Fumitoshi Sakata, Tokyo (JP); Takumi Tokiyoshi, Tokyo (JP); Yasuharu Chuman, Tokyo (JP); Takuya Fukahori, Tokyo (JP); Yuichi Kanemaki, Tokyo (JP); Hiroyuki Ohyama, Tokyo (JP); Shintaro Matsumoto, Tokyo (JP); Masaaki Fujita, Tokyo (JP); Ichiro Ohtsu, Tokyo (JP)

(73) Assignee: MITSUBISHI HITACHI POWER SYSTEMS, LTD., Kanagawa (JP)

( * ) Notice: Subject to any disclaimer, the term of this patent is extended or adjusted under 35 U.S.C. 154(b) by 96 days.

(21) Appl. No.: 14/781,357

(22) PCT Filed: Jan. 15, 2015

(86) PCT No.: PCT/JP2015/050882
§ 371 (c)(1),
(2) Date: Sep. 30, 2015

(87) PCT Pub. No.: WO2015/174101
PCT Pub. Date: Nov. 19, 2015

(65) Prior Publication Data
US 2016/0208978 A1    Jul. 21, 2016

(51) Int. Cl.
*G01N 3/20* (2006.01)
*F16L 57/06* (2006.01)
(Continued)

(52) U.S. Cl.
CPC .............. *F16L 57/06* (2013.01); *F16L 13/06* (2013.01); *F16L 53/00* (2013.01); *F16L 57/00* (2013.01);
(Continued)

(58) Field of Classification Search
CPC . F16L 57/06; F16L 13/06; F16L 53/00; F16L 57/00; F16L 58/02; F16L 59/20;
(Continued)

(56) References Cited

U.S. PATENT DOCUMENTS 6,606,910 B1 *  8/2003  Nishimura ........... G01N 29/069
                                                    73/599
6,810,748 B1 * 11/2004  Nishida .................. G01N 33/20
                                                    356/32
(Continued)

FOREIGN PATENT DOCUMENTS

CN    103765192      4/2014
JP    9-292064      11/1997
(Continued)

OTHER PUBLICATIONS

Office Action issued Sep. 5, 2016 in Taiwanese Application No. 104102558, with English translation.
(Continued)

*Primary Examiner* — Max Noori
(74) *Attorney, Agent, or Firm* — Wenderoth, Lind & Ponack, L.L.P.

(57) ABSTRACT

A method of extending a life expectancy of a high-temperature piping, includes removing a heat insulation material which covers the piping having a high creep rupture risk, and lowering an outer surface temperature of piping, wherein a width of an exposed portion obtained is twice or more a distance from a peeled-off end portion of the exposed
(Continued)

portion to a portion where a compressive stress is asymptotical to 0 after a change in stress between a tensile stress and the compressive stress occurring in the piping due to the removal of the heat insulation material is made from the tensile stress to the compressive stress, and the distance is calculated based on the following formulae, βx=5, $$\beta = \sqrt[4]{\frac{3(1-v^2)}{a^2 h^2}}$$

here, v is a Poisson's ratio, a is an average radius of the piping, and h is a plate thickness of the piping.

10 Claims, 6 Drawing Sheets

(51) Int. Cl.
  *F16L 57/00*   (2006.01)
  *G01N 17/00*   (2006.01)
  *F16L 59/20*   (2006.01)
  *F16L 13/06*   (2006.01)
  *F16L 53/00*   (2006.01)
  *G01N 33/20*   (2006.01)
  *F16L 58/02*   (2006.01)
  *G21C 17/017*   (2006.01)
  *G21D 1/00*   (2006.01)

(52) U.S. Cl.
  CPC ............. *F16L 58/02* (2013.01); *F16L 59/20* (2013.01); *G01N 17/00* (2013.01); *G01N 33/20* (2013.01); *G21C 17/017* (2013.01); *G21D 1/00* (2013.01)

(58) Field of Classification Search
  CPC ...... G01N 17/00; G01N 33/20; G21C 17/017; G21D 1/00
  USPC .................................................. 73/850, 851
  See application file for complete search history.

(56) References Cited

U.S. PATENT DOCUMENTS

| | | | |
|---|---|---|---|
| 7,283,929 B2* | 10/2007 | Fujiyama | G05B 23/0216 702/182 |
| 2009/0056839 A1 | 3/2009 | Aoike et al. | |
| 2010/0035008 A1* | 2/2010 | Backman | C08L 23/06 428/36.9 |
| 2012/0136589 A1 | 5/2012 | Ogawa et al. | |
| 2012/0183114 A1* | 7/2012 | Bischoff | F16L 55/32 376/248 |

FOREIGN PATENT DOCUMENTS

| | | |
|---|---|---|
| JP | 11-22893 | 1/1999 |
| JP | 2002-38219 | 2/2002 |
| JP | 2003-113989 | 4/2003 |
| JP | 3435504 | 6/2003 |
| JP | 2004-85347 | 3/2004 |
| JP | 2008-122345 | 5/2008 |
| JP | 2010-236941 | 10/2010 |
| JP | 2014-126402 | 7/2014 |
| JP | 5701349 | 2/2015 |
| JP | 2015-45619 | 3/2015 |
| TW | I339683 | 4/2011 |
| WO | 2011/078333 | 6/2011 |

OTHER PUBLICATIONS

Notice of Acceptance issued Aug. 2, 2016 in Australian Application No. 2015224531.
International Search Report issued Apr. 14, 2015 in International (PCT) Application No. PCT/JP2015/050882.
Decision of a Patent Grant issued Jan. 20, 2015 in Japanese Application No. 2013-178299, with English translation.
Written Opinion of the International Searching Authority issued Apr. 14, 2015 in International (PCT) Application No. PCT/JP2015/050882, with English translation.
Patent Examination Report issued Jun. 17, 2016 in corresponding Australian Application No. 2015224531.
Extedned European Search Report issued Jun. 9, 2016 in European Application No. 15762469.3.
Communication under Rule 71(3) EPC issued Dec. 14, 2017 in corresponding European Application No. 15 762 469.3.

\* cited by examiner

METHOD OF EXTENDING LIFE EXPECTANCY OF HIGH-TEMPERATURE PIPING AND LIFE EXPECTANCY EXTENSION STRUCTURE OF HIGH-TEMPERATURE PIPING

BACKGROUND OF THE INVENTION

1. Technical Field

The present invention relates to a method of extending a life expectancy of a high-temperature piping such as a high-temperature piping and a pressure vessel, for example, used in thermal and nuclear power plants, chemical plants and the like, and a life expectancy extension structure of a high-temperature piping.

2. Description of the Related Art

Since, for example, a boiler or the like constituting a thermal power plant is operated under a high-temperature and high-pressure environment, damage due to creep or the like may accumulate in a heat-resistant steel as a material forming the boiler, by being operated over a long term. Accordingly, at the time of operation of this type of plant, it is important to maintain the reliability of a pressure-resistant unit by performing the highly accurate life expectancy evaluation of the heat-resistant steel in ensuring a stable operation over a long term.

Although a high-temperature piping used in a thermal power plant or the like has a function of carrying steam heated in the boiler to a steam turbine, a creep damage progresses due to the high-temperature and the long-term use and a creep void occurs, a crack occurs due to continuous voids, and finally, the piping breaks.

In order to prevent the final breakage, a degree of creep damage of each member is derived by analyzing a degree of growth of the creep void through a regular non-destructive inspection, thereby performing the remaining life expectancy evaluation of the member (see Japanese Laid-open Patent Publication No. 2004-85347; and Japanese Laid-open Patent Publication No. 2008-122345). Since there is a high risk of creep rupture of the piping welded portion in general compared to a base metal, a position to be inspected is mainly a welded portion.

SUMMARY OF THE INVENTION

1. Technical Problem

When there is a member with a high degree of creep damage as a result of the non-destructive inspection, and thus the risk of the creep rupture is high until the next regular inspection, measures are taken to reduce the creep rupture risk, by performing replacement of the member or by lowering the operating temperature of the overall plant to lower the metal temperature of the overall piping.

However, when lowering the overall operating temperature of the plant, there is a problem of a decrease in the operating efficiency of the plant.

Thus, there is an earnest desire to develop a technique that is capable of extending the remaining life expectancy of the high-temperature member, without lowering the overall operating temperature of the plant, and without lowering the operating efficiency of the plant.

An object of the present invention is to provide a method of extending a life expectancy of a high-temperature piping and a life expectancy extension structure of the high-temperature piping capable of extending the remaining life expectancy of the high-temperature member, without lowering the overall operating temperature of the plant, and without lowering the operating efficiency of the plant.

2. Solution to the Problem

A first aspect of the present invention to solve the problems described above is a method of extending a life expectancy of a high-temperature piping, and includes, when it is determined that a continued stationary use cannot be performed by a remaining life expectancy evaluation of a creep rupture of a welded portion of the high-temperature piping, removing a part of a heat insulation material which covers a location having a high creep rupture risk in the high-temperature piping, and lowering an outer surface temperature of the high-temperature piping locally to extend the life expectancy of the location having the high creep rupture risk, wherein a width of an exposed portion obtained by removing a part of a heat insulation material is twice or more a distance from a peeled-off end portion of the exposed portion to a portion where a compressive stress is asymptotical to 0 after a change in stress between a tensile stress and the compressive stress occurring in the high-temperature piping due to the removal of the heat insulation material is made from the tensile stress to the compressive stress, and the distance at which the compressive stress after a change in stress is made from the tensile stress to the compressive stress is asymptotical to 0 is based on the following formula (1), $$\beta x = 5 \qquad (1)$$

β is expressed by the following formula (2), $$\beta = \sqrt[4]{\frac{3(1-\nu^2)}{a^2 h^2}} \qquad (2)$$

here, ν is a Poisson's ratio, and symbol a is an average radius of the piping, and symbol h is a plate thickness of the piping.

A second aspect of the invention is the method of extending the life expectancy of the high-temperature piping in the first aspect of the invention, in which the surface of the member on which the heat insulation material has been removed is cooled.

A third aspect of the invention is the method of extending the life expectancy of the high-temperature piping in the second aspect of the invention, in which the cooling is cooling by air or cooling by cooling water.

A fourth aspect of the invention is the method of extending the life expectancy of the high-temperature piping in the first aspect of the invention, in which a heat dissipating member is installed on the surface of the member on which the heat insulation material has been removed.

A fifth aspect of the invention is the method of extending the life expectancy of the high-temperature piping in the first aspect of the invention, in which the temperature of the surface of the member on which the heat insulation material has been removed is measured to determine that the cooling capacity is appropriate.

A sixth aspect of the invention is the method of extending the life expectancy of the high-temperature piping in the fifth aspect of the invention, in which, when the cooling capacity is not appropriate, the cooling capacity is changed to be appropriate.

A seventh aspect of the invention is a life expectancy extension structure of a high-temperature piping, includes, when it is determined that a continued stationary use cannot be performed by a remaining life expectancy evaluation of a creep rupture of the high-temperature piping, removing a part of a heat insulation material that covers a location having a high creep rupture risk in the high-temperature piping, lowering an outer surface temperature of the high-temperature piping locally, wherein a width of an exposed portion obtained by removing a part of a heat insulation material is twice or more a distance from a peeled-off end portion of the exposed portion to a portion where a compressive stress is asymptotical to 0 after a change in stress between a tensile stress and the compressive stress occurring in the high-temperature piping due to the removal of the heat insulation material is made from the tensile stress to the compressive stress, and the distance at which the compressive stress after a change in stress is made from the tensile stress to the compressive stress is asymptotical to 0 is based on the following formula (1), $$\beta x = 5 \quad (1)$$

β is expressed by the following formula (2), $$\beta = \sqrt[4]{\frac{3(1-v^2)}{a^2 h^2}} \quad (2)$$

here, v is a Poisson's ratio, and symbol a is an average radius of the piping, and symbol h is a plate thickness of the piping.

An eighth aspect of the invention is the life expectancy extension structure of the high-temperature piping in the seventh aspect of the invention, including a cooling unit that cools a surface of the member on which the heat insulation material has been removed.

A ninth aspect of the invention is the life expectancy extension structure of the high-temperature piping in the eighth aspect of the invention, in which the cooling unit is an air-cooling unit by air or a water-cooling unit by cooling water.

A tenth aspect of the invention is the life expectancy extension structure of the high-temperature piping in the seventh aspect of the invention, in which a heat dissipating member is installed on the surface of the member on which the heat insulation material has been removed.

3. Advantageous Effects of Invention

According to the present invention, by lowering the metal temperature of the piping, the creep rupture life expectancy of the piping is extended, and it is possible to extend the remaining life expectancy of the piping.

DETAILED DESCRIPTION OF THE INVENTION

Preferred embodiments of the present invention will be described in detail with reference to the accompanying drawings. The present invention is not intended to be limited by the embodiments, and when there are plural embodiments, the present invention also includes a configuration in which the embodiments are combined with one another.

First Embodiment

Figure 1:
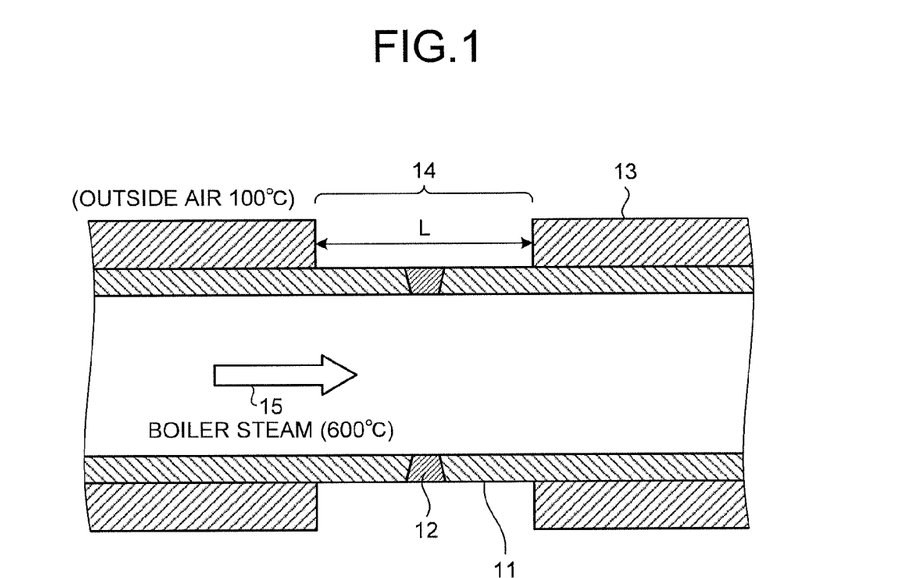
FIG. 1 is a schematic diagram of a life expectancy extension structure of a high-temperature piping according to a first embodiment.

FIG. 1 is a schematic diagram of a life expectancy extension structure of a high-temperature piping according to a first embodiment.

As illustrated in FIG. 1, according to a life expectancy extension structure of a high-temperature piping according to the present embodiment, when a location having a high creep rupture risk (a weld portion having a high degree of creep damage) is checked and it is determined that the continued stationary use cannot be performed, by a remaining life expectancy evaluation of a creep rupture of a welded portion 12 of a high-temperature piping (hereinafter, referred to as "piping") 11 as a high-temperature member, a part of a heat insulation material 13 covering the location having the high creep rupture risk in the piping 11 is removed in a direction of rotation to form an exposed portion 14, an outer surface temperature of the piping 11 is locally lowered, and the extension of the life expectancy of the creep rupture location is achieved.

In FIG. 1, reference numeral 15 illustrates a boiler steam, for example, a high-temperature steam of 600° C. flows through the piping 11.

In the welded portion 12 of the piping 11 which is determined to have a high creep rupture risk by the non-destructive inspection, by removing the heat insulation material 13 that is permanently installed to form an exposed portion 14 as illustrated in FIG. 1, the heat is released from the exposed portion 14, and thus the metal temperature of the piping 11 is lowered.

In this case, by removing the heat insulation material 13 to form the exposed portion 14, the natural convection heat transfer with the outside air (for example, 100° C.) is made, and the heat transfer coefficient becomes about 2 to 12 W/m²K.

In this way, by lowering the metal temperature of the piping 11, the creep rupture life expectancy of the piping 11 is extended, and it is possible to extend the remaining life expectancy of the piping.

As a result, since it is possible to achieve the extension of life expectancy only by a local drop in the temperature of the piping, it is possible to solve harmful effects that the metal temperature of the overall piping is lowered by lowering the operating temperature of the overall plant, and the operating efficiency of the plant is reduced due to a reduction in the creep rupture risk, as in the related art.

In this way, according to this embodiment, when a location having a high creep damage risk in the high-temperature piping is checked, by removing the heat insulation material 13 that covers the piping 11 only by a width (L) of a predetermined distance to form an exposed portion 14, the metal temperature is lowered to reduce the creep damage risk, and thus, it is possible to achieve the extension of life expectancy, without reducing the operating efficiency of the overall plant. Here, the reduction in the metal temperature is also effective in the extension of the crack growth life expectancy, as well as the creep rupture life expectancy.

Here, when an outer diameter of the piping 11 is, for example, 460 mm, the width L of removing the heat insulation material 13 is preferably within a range of approximately 900 mm or more as described below. However, depending on the width of removing the heat insulation material 13, it is also possible to generate a compressive stress by the local surface outward deformation and to expect the extension of life expectancy due to the stress reduction.

Then, the width L of removing a part of the heat insulation material 13 will be described.

Figure 2:
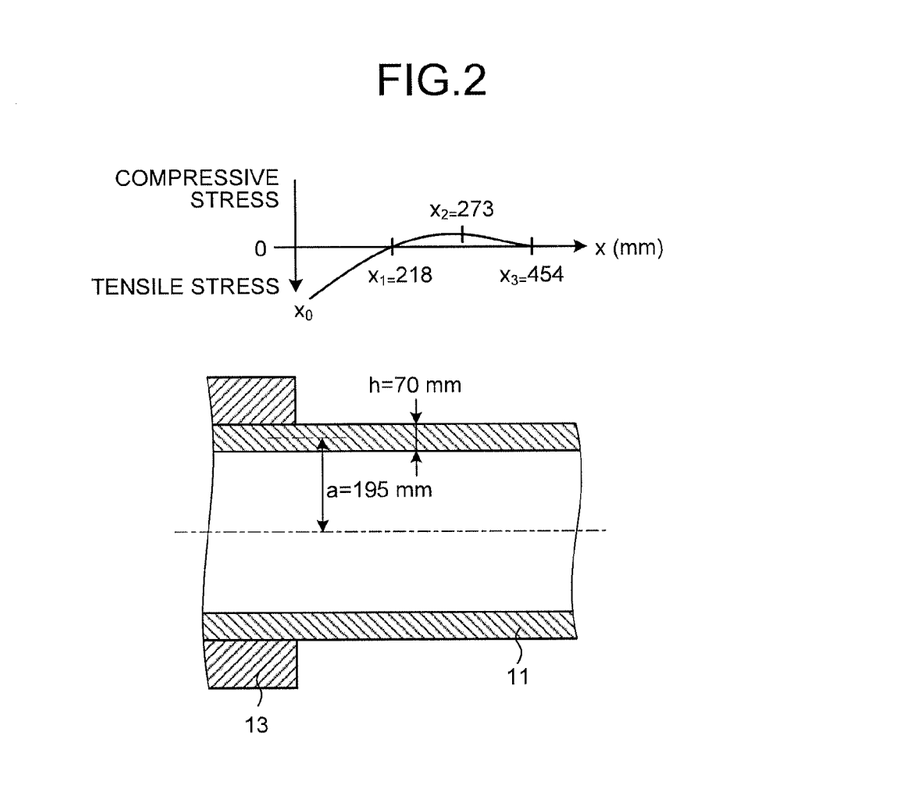
FIG. 2 is a diagram illustrating a portion of a piping in which a heat insulation material is peeled off.

In FIG. 2, a distance (L/2) from an end $x_0$ at which the heat insulation material 13 is removed in a state where the left portion of the heat insulation material 13 is removed from the piping 11 to the heat insulation material 13 to be removed, will be described.

Since the tensile stress and the compressive stress are applied to the piping 11 by removing the heat insulation material 13, when the distance from the location $x_0$ in which the heat insulation material 13 is peeled off is set to x ($x_1$, $x_2$ and $x_3$), the distance in which a change in stress is asymptotic to 0 is expressed by the following formula.

$$\beta x = 5 \quad (1)$$

Here, since $\beta$ is expressed by the following formula (2), the value of x may be obtained.

$$\beta = \sqrt[4]{\frac{3(1-v^2)}{a^2 h^2}} \quad (2)$$

Here, v is material characteristics such as a Poisson's ratio, and a metal material of the general piping 11 is approximately 0.3. Also, symbol a is an average radius, and symbol h is a plate thickness.

For example, when the outer diameter of the piping 11 is 460 mm and the plate thickness is 70 mm, a is 195 mm, and h is 70 mm, the value of x at the time of $\beta x = 2.4$ is 218 mm, and the value of x is 454 mm at the time of $\beta x = 5$. In addition, since $\beta \propto 1/\sqrt{(ah)}$, the value of x and $\sqrt{(ah)}$ become associated values, and when a and h are changed, the value of x is changed.

Thus, for example, when then outer diameter is 460 mm and the plate thickness is 70 mm, x becomes 218 to 454 mm.

The distance (L) in which the heat insulation material 13 is peeled off to form the exposed portion 14 of the piping 11 will be described with reference to FIGS. 2 and 3.

FIG. 2 is a diagram illustrating a portion of the piping in which the heat insulation material is peeled off. Although the heat insulation material is peeled off around the welded portion, FIG. 2 illustrates the left peeled-off portion.

Figure 3:
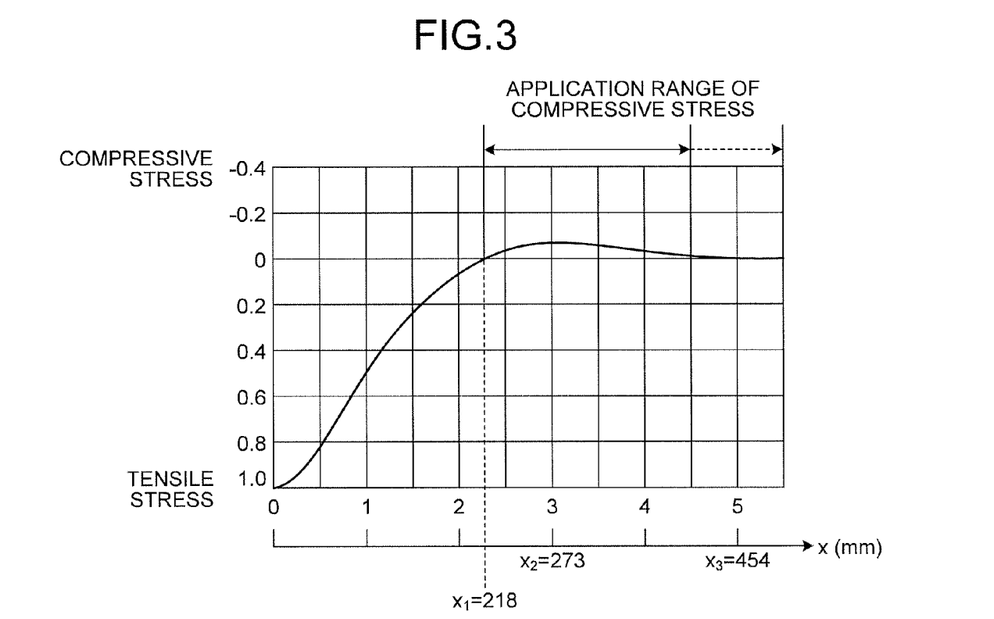
FIG. 3 is a diagram illustrating a relation among a distance from a location at which the heat insulation material is peeled off, and a tensile stress and a compressive stress applied to an interior of piping.

FIG. 3 is a diagram illustrating a relation among the distance (mm) from the location $x_0$ at which the heat insulation material is peeled off, and a tensile stress and a compressive stress applied to in the interior of the piping.

In the piping of FIG. 2, the description will be given of a case where the outer diameter of the piping is 460 mm, and the plate thickness of the piping is 70 mm.

As illustrated in FIG. 3, when the location 0 mm of the piping at which the heat insulation material is peeled off is set to $x_0$, as described above, the tensile stress at a predetermined distance $x_1$ (=218 mm) is zero. The compressive stress becomes maximum at a predetermined distance $x_2$ (=273 mm) further from the predetermined distance $x_1$. The compressive stress becomes zero and converges at a further predetermined distance $x_3$ (=454 mm) from the predetermined distance $x_2$.

When combining the left peeled-off portion of the piping 11 with the right peeled-off portion, the peeled-off portion becomes twice, so that the distance L to be peeled off becomes 454 mm×2=908 mm.

Thus, the distance L to be peeled off is preferably set to approximately 900 mm or more.

Also, in the case of achieving further the extension of life expectancy by the compressive stress, the range of removing the heat insulation material 13 may be determined based on the following formula (3).

$$2.4 \leq \beta x < 5 \quad (3)$$

For example, in the case of the outer diameter of 460 mm and the plate thickness of 70 mm, it is necessary to peel off the heat insulation material at least by a distance $x_1$ (=218 mm) in which the tensile stress is not applied, and there is no need to peel off the heat insulation material at the converging distance $x_3$ (454 mm) or more.

Second Embodiment

Figure 4:
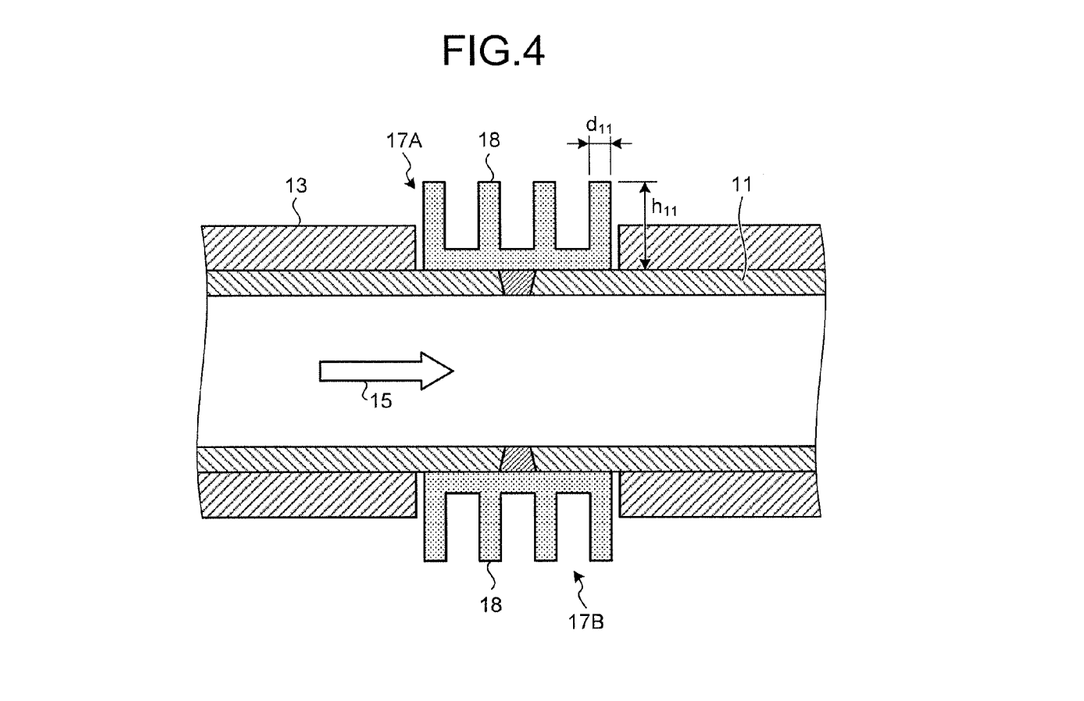
FIG. 4 is a schematic diagram of a life expectancy extension structure of a high-temperature piping according to a second embodiment.
Figure 5:
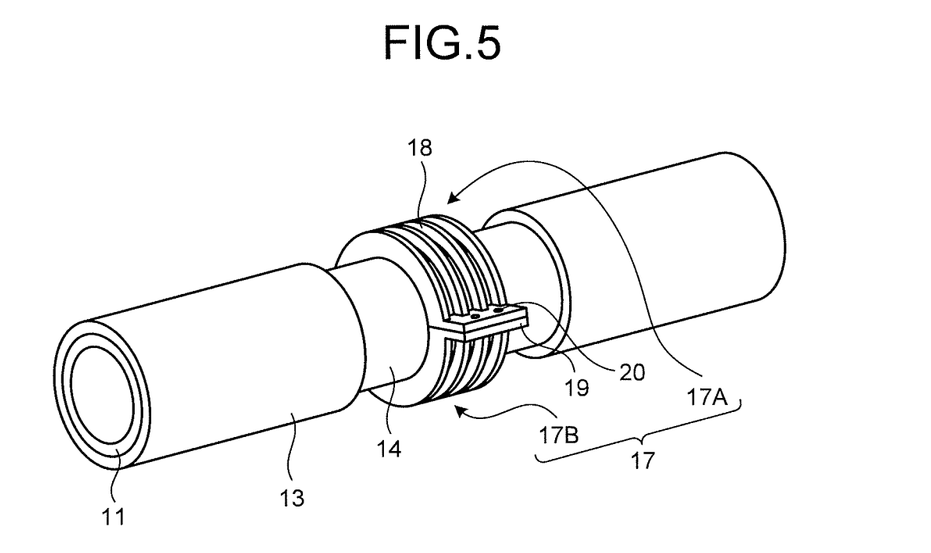
FIG. 5 is a perspective view of FIG. 4.

FIG. 4 is a schematic diagram of a life expectancy extension structure of a high-temperature piping according to a second embodiment. FIG. 5 is a perspective view of FIG. 4. In addition, the same members as those of the configuration according to the first embodiment are denoted by the same reference numerals, and the descriptions thereof will be omitted. As illustrated in FIGS. 4 and 5, a life expectancy extension structure of a high-temperature piping according to the second embodiment is provided so that a multi-layered fin 17 serving as a heat dissipating member comes into close contact with respect to a circumference of an exposed portion 14 obtained by removing a heat insulation material 13 in the first embodiment.

As illustrated in FIG. 5, an upper fin 17A having a plurality of fins 18 and a lower fin 17B having a plurality of fins 18 are fastened by a fastening member 20 by combining flanges 19 each other.

A thickness ($d_{11}$) of the fin 18 is, for example, 70 mm, and a height ($h_{11}$) is about 300 mm to form a multi-layered fin structure.

In this embodiment, in the welded portion of the high-temperature piping which is determined to have a high creep rupture risk by the non-destructive inspection, by removing the heat insulation material 13 that is permanently installed as illustrated in FIGS. 4 and 5 to form the exposed portion 14, and the upper fin 17A and the lower fin 17B are installed so as to come into close contact with the exposed portion 14. Thus, it is possible to lower the metal temperature of the piping than that of the first embodiment, by increasing the area of releasing the heat using the multi-layered fin structure.

According to this embodiment, the heat insulation material 13 is removed, the area of releasing the heat is increased by the multi-layered fin 17 installed in the exposed portion 14, the heat flux increases in proportion to the area increase rate, and it is possible to quickly cool the metal temperature as compared to the first embodiment.

As a result, the creep rupture life expectancy of the piping 11 is extended by lowering the metal temperature, and it is possible to extend the remaining life expectancy of the piping.

Figure 6:
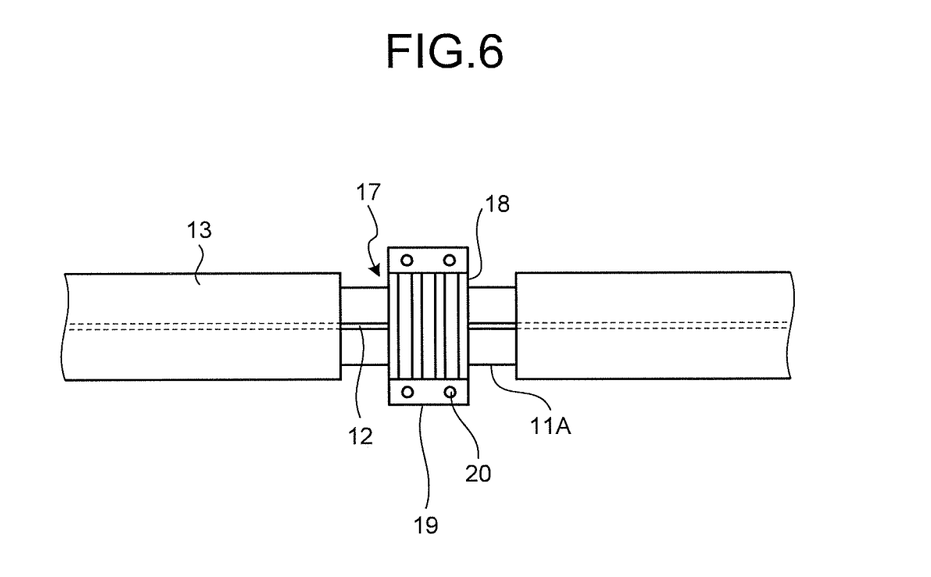
FIG. 6 is a schematic diagram of a life expectancy extension structure of another high-temperature piping according to the second embodiment.

FIG. 6 is a schematic diagram of the life expectancy extension structure of another high-temperature piping according to a second embodiment.

As illustrated in FIG. 6, a multi-layered fin 17 is installed in a longitudinal joint piping 11A by a longitudinal welded portion 12. Thus, by increasing the heat flux at the installation of the multi-layered fin 17 and by cooling the piping by the natural convection heat transfer with the outside air, compressive stress is added to the piping 11 by the thermal expansion difference between the multi-layered fin 17 and the piping 11, and it is possible to achieve a stress reduction effect.

Third Embodiment

Figure 7:
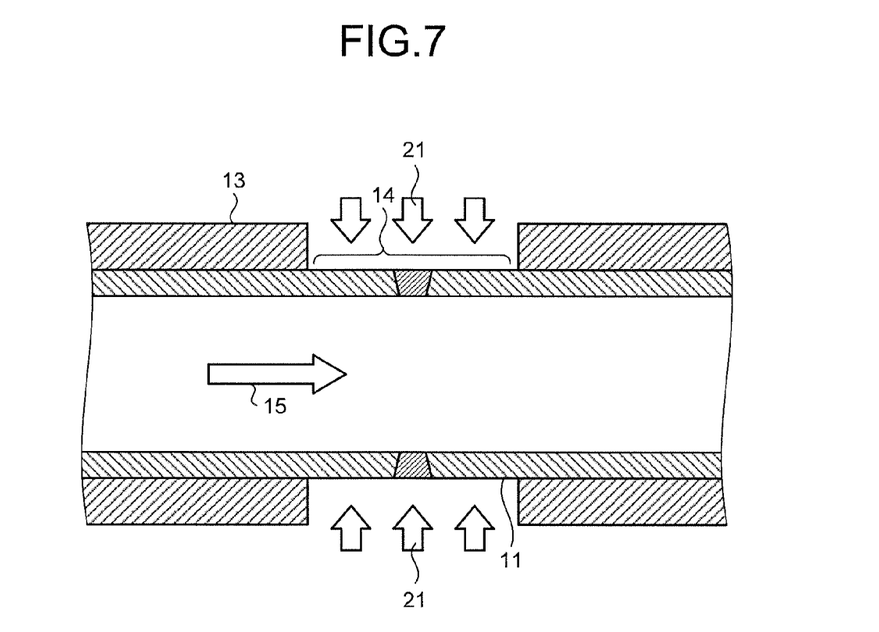
FIG. 7 is a schematic diagram of a life expectancy extension structure of a high-temperature piping according to a third embodiment.

FIG. 7 is a schematic diagram of a life expectancy extension structure of a high-temperature piping according to a third embodiment. In addition, the same members as those of the configuration according to the first embodiment are denoted by the same reference numerals, and the description thereof will not be provided. As illustrated in FIG. 7, in the life expectancy extension structure of the high-temperature piping according to the third embodiment, the surface of the exposed portion 14 obtained by removing the heat insulation material 13 in the first embodiment is cooled by a cooling medium (for example, air) 21. Here, as the cooling medium 21, it is also possible to use a chore effluent gas, an inert gas or the like other than air.

Figure 8:
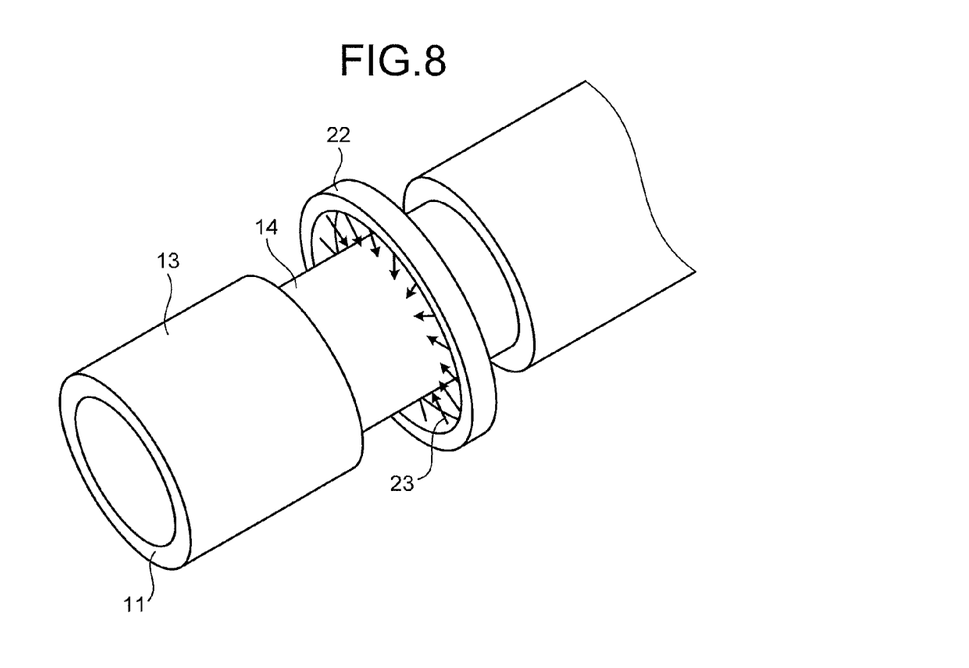
FIG. 8 is a perspective view illustrating an example of an air supply unit that supplies a cooling air.

FIG. 8 is a perspective view illustrating an example of an air supply unit that supplies the cooling air.

As illustrated in FIG. 8, an annular air supply unit 22 is provided along an outer periphery of the exposed portion 14 of the piping 11 to blow an air 23 over the overall periphery from an air injection hole (not illustrated) of the annular air supply unit 22, thereby performing the forced cooling.

The wind velocity of the air forcibly cooled by the cooling medium 21 is preferably, for example, approximately 10 m/s.

In the welded portion of the high-temperature piping which is determined to have the high creep rupture risk by the non-destructive inspection, as illustrated in FIGS. 7 and 8, by removing the heat insulation material 13 which is permanently installed and forcibly cooling the welded portion by the cooling medium (air) 21, heat is dissipated, thereby lowering the metal temperature of the piping 11.

In this case, by removing the heat insulation material 13 and performing the forced cooling on the exposed portion 14 by the cooling medium (air) 21, the forced convection heat transfer with the outside air is performed, and the heat transfer rate becomes approximately 20 to 100 W/m²K.

In the third embodiment, unlike the first and second embodiments, by forcibly lowering the metal temperature by the cooling medium 21, the creep rupture life expectancy of the piping 11 is extended, and it is possible to extend the remaining life expectancy of the piping.

Fourth Embodiment

Figure 9:
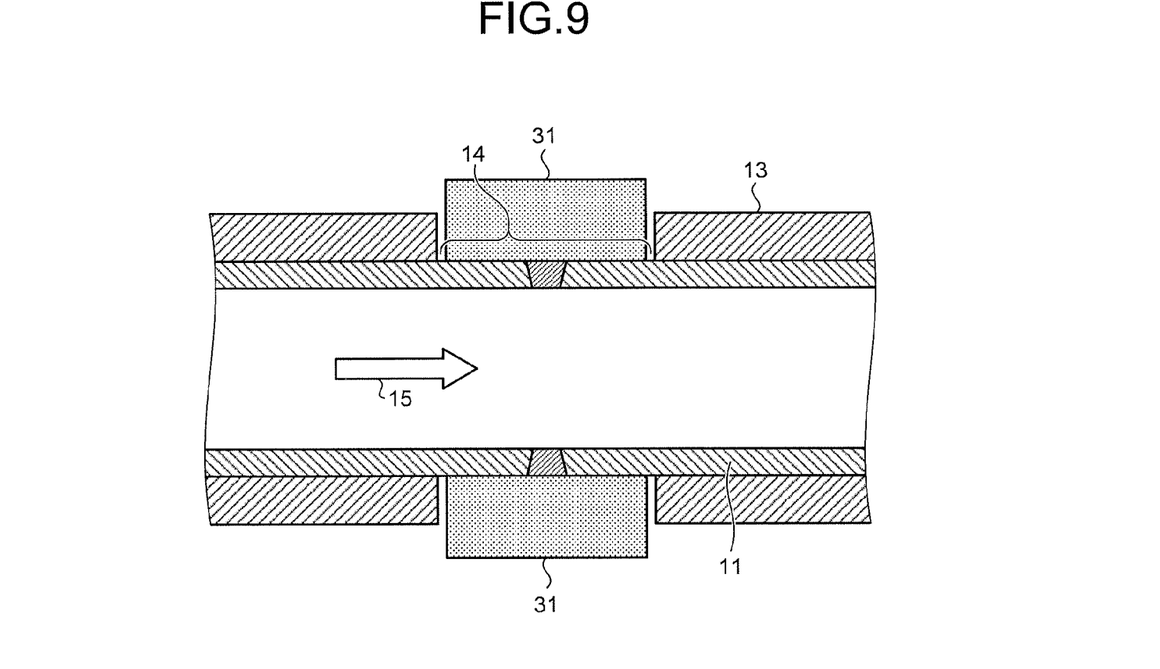
FIG. 9 is a schematic diagram of a life expectancy extension structure of a high-temperature piping according to a fourth embodiment.

FIG. 9 is a schematic diagram of a life expectancy extension structure of a high-temperature piping according to a fourth embodiment. In addition, the same members as those of the configuration according to the first embodiment are denoted by the same reference numerals, and the description thereof will be omitted. As illustrated in FIG. 9, in the life expectancy extension structure of the high-temperature piping according to the fourth embodiment, a water jacket 31 serving as a cooling unit is provided around the exposed portion 14 obtained by removing the heat insulation material 13 in the first embodiment. By installing the water jacket 31 to cool the piping by the natural heat transfer with the water, heat exchange with the internal fluid is performed to reduce the metal temperature.

In the welded portion of the piping which is determined to have the high creep rupture risk by the non-destructive inspection, as illustrated in FIG. 9, by removing the heat insulation material 13 that is permanently installed, and by forcibly releasing the heat using the water jacket 31 or the like, the metal temperature of the piping is lowered.

In this case, the natural convection heat transfer with the cooling water is performed by removing the heat insulation material 13 and by disposing the water jacket 31 in the exposed portion 14, and the heat transfer rate becomes approximately 500 to 600 W/m²K. As a result, the metal temperature is lowered, the creep rupture life expectancy of the piping 11 is extended, and it is possible to extend the remaining life expectancy of the piping.

Figure 10:
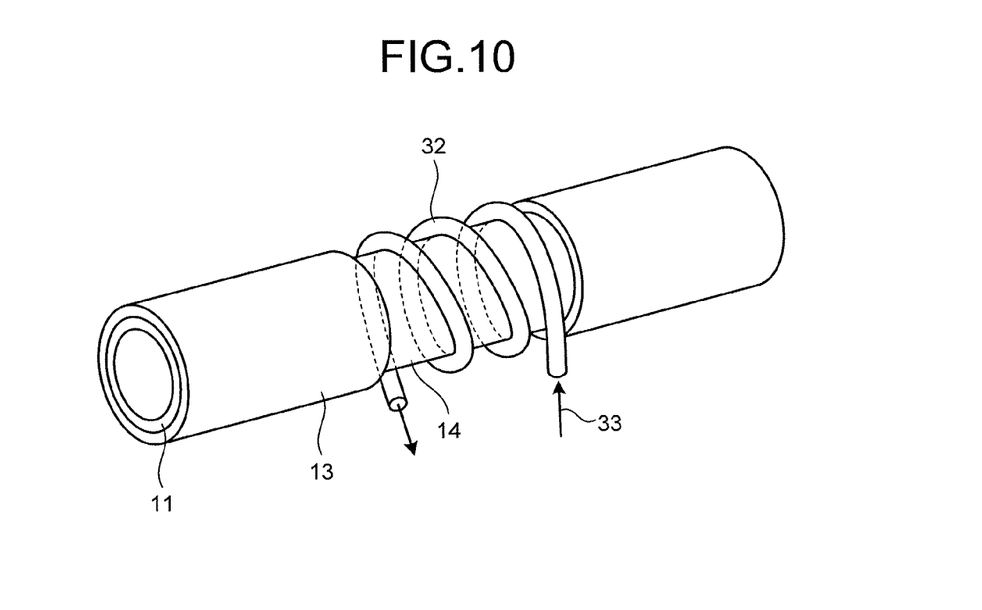
FIG. 10 is a schematic diagram of a life expectancy extension structure of another high-temperature piping according to the fourth embodiment.

FIG. 10 is a schematic diagram of the life expectancy extension structure of another high-temperature piping according to the fourth embodiment.

In FIG. 10, a cooling piping 32 is disposed on the surface of the exposed portion 14 obtained by removing the heat insulation material 13, and heat is dissipated by a cooling water 33 by causing the cooling water 33 to flow therethrough to achieve a reduction in the metal temperature of the piping 11.

The velocity of the cooling water 33 for the forced cooling is preferably, for example, approximately 1 m/s. In addition, the diameter of the cooling piping 32 to be wound may be, for example, about 20 mm.

Figure 11:
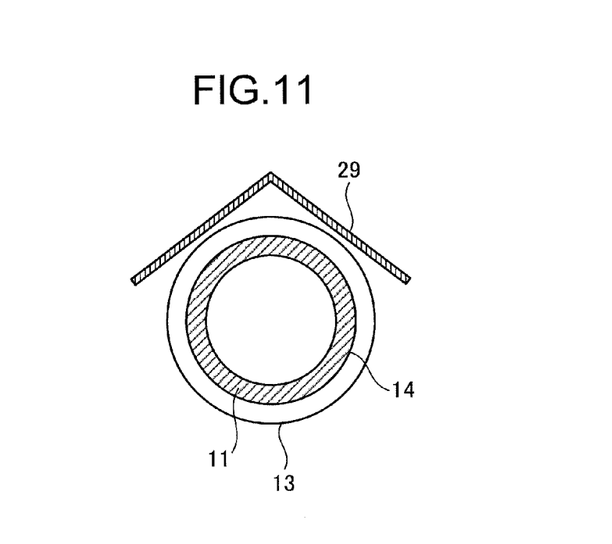
FIG. 11 is a schematic diagram of a protective structure of an exposed portion of the high-temperature piping.

FIG. 11 is a schematic diagram of a protective structure of the exposed portion of the high-temperature piping.

Further, as illustrated in FIG. 11, in order to prevent a state in which the exposed portion 14 is exposed to rain due to the removable of the heat insulation material 13 of the piping 11, it is preferred to install the protective member 29, such as flashing, over a range that is longer than a range L of the exposed portion 14 so as not to be a thermal barrier with respect to the piping 11. Furthermore, by installing the protective member 29 other than the thermal barrier measures, the thermal influence due to sun is prevented to secure the proper cooling.

Fifth Embodiment

Figure 12:
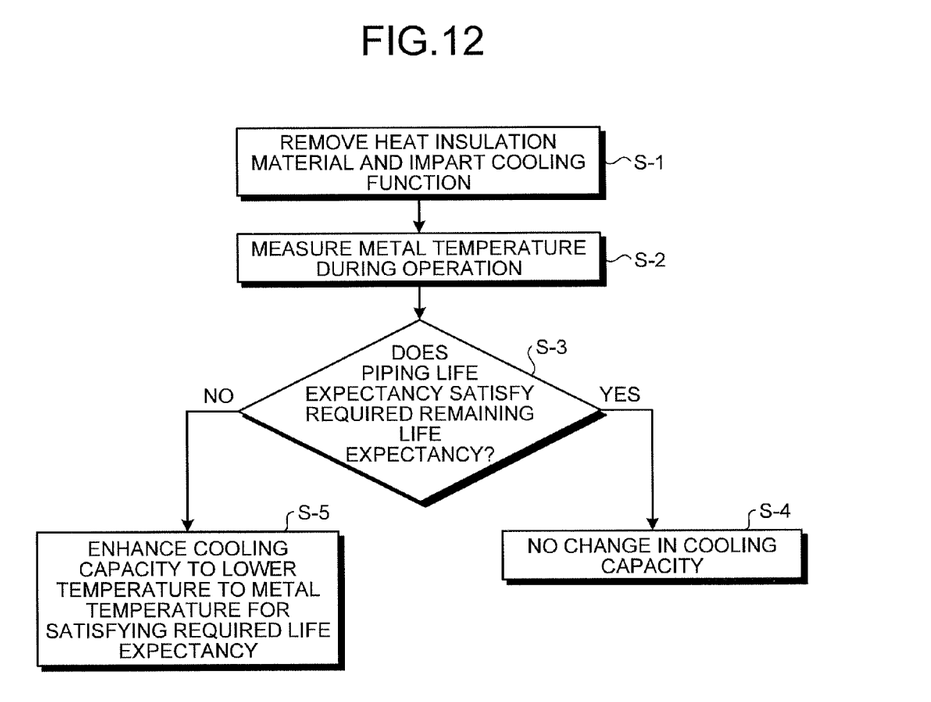
FIG. 12 is a process diagram of a method of controlling a metal temperature of the high-temperature piping.

FIG. 12 is a process diagram of a method of controlling a metal temperature of the high-temperature piping.

In this embodiment, when cooling the piping by the cooling unit such as the cooling medium 21 and the cooling water, the temperature of the surface of the piping on which the heat insulation material 13 has been removed is measured by the temperature measuring unit, and it is determined that the cooling capacity is appropriate.

In the welded portion of the high-temperature piping which is determined to have the high creep rupture risk by the non-destructive inspection, after removing the heat insulation material 13 that is permanently installed, a thermocouple of the temperature measuring unit is attached to a part of the exposed portion 14 to measure the metal temperature of the piping 11 and evaluate the remaining life expectancy. It is preferred that the installation of the thermocouple be installed at a plurality of positions spaced away from the thermally affected portion by 10 to 20 mm.

In this case, it is possible to determine whether the required remaining life expectancy can be achieved by measuring the temperature, and by combining the forced cooling due to the blowing of the third embodiment with the water jacket of the fourth embodiment, it is possible to control the cooling capacity so as to satisfy the required remaining life expectancy, thereby extending the life expectancy of the piping.

For example, if the remaining time until the next periodical check is 10,000 hours, in a case where the forced cooling is performed by the cooling water 33 in the cooling piping 32 wound as illustrated in FIG. 10, and it is determined that there is a need to lower the temperature by approximately 50° C., if the temperature decreases only by 30° C. through the temperature measurement in the cooling due to the actual cooling water 33, by performing the cooling that further lowers the temperature by the insufficient temperature of 20° C., for example, by performing the forced cooling due to the air cooling or the control (control such as further lowering the temperature of the cooling water by the coolant) of the cooling capacity of the cooling medium, it is possible to extend the life expectancy of the piping so as to have a required remaining life expectancy.

Then, a process of a method of controlling the metal temperature of such a high-temperature piping will be described with reference to FIG. 12.

In a first step, in the welded portion of the piping which is determined to have the high creep rupture risk by the non-destructive inspection, the heat insulation material 13 of the piping 11 is removed to impart a cooling function of the third or fourth embodiment (S-1).

In a second step, the metal temperature of the exposed portion 14 of the piping 11 is measured during operation (S-2).

As a determination of a result of the temperature measurement of the second step (S-2), it is determined whether the piping life expectancy satisfies the required remaining life expectancy by the temperature measurement (S-3).

In a third step (S-3), in the case of satisfying the remaining life expectancy (Yes), the operation is performed as it is without changing the cooling capacity (S-4).

In contrast, in a third step (S-3), when the remaining life expectancy is not satisfied (No), an operation of lowering the temperature to the metal temperature for satisfying the required life expectancy is performed by enhancing the cooling capacity (S-5).

As a result, it is possible to implement a sound operation until the remaining life expectancy.

Also, by performing the temperature measurement, it is possible to determine whether the current cooling is sound.

REFERENCE SIGNS LIST

11 High-Temperature Piping (Piping)
12 WELDED PORTION
13 Heat Insulation Material
14 Exposed Portion
15 Boiler Steam

The invention claimed is:

1. A method of extending a life expectancy of a high-temperature piping, comprising:
when it is determined that a continued stationary use cannot be performed by a remaining life expectancy evaluation of a creep rupture of a welded portion of the high-temperature piping,
peeling off a part of a heat insulation material from an outer surface of the high-temperature piping, which covers a location having a high creep rupture risk in the high-temperature piping, to form an exposed portion of the high-temperature piping; and
lowering an outer surface temperature of the high-temperature piping locally to extend the life expectancy of the location having the high creep rupture risk,
wherein a width of the exposed portion of the heat insulation material is twice or more a distance from an end portion of the exposed portion to a portion where a compressive stress is asymptotical to 0 after a change in stress between a tensile stress and the compressive stress occurring in the high-temperature piping due to the removal of the heat insulation material is made from the tensile stress to the compressive stress, and
the distance at which the compressive stress after a change in stress is made from the tensile stress to the compressive stress is asymptotical to 0 is based on the following formula (1), $$\beta x = 5 \qquad (1)$$

$\beta$ is expressed by the following formula (2), $$\beta = \sqrt[4]{\frac{3(1-v^2)}{a^2 h^2}} \qquad (2)$$

here, x is a distance from the end portion of the exposed portion, v is a Poisson's ratio, and symbol a is an average radius of the piping, and symbol h is a plate thickness of the piping.

2. The method of extending the life expectancy of the high-temperature piping according to claim 1, wherein the outer surface of the high-temperature piping, from which the heat insulation material has been removed, is cooled.

3. The method of extending the life expectancy of the high-temperature piping according to claim 2, wherein the cooling is cooling by air or cooling by cooling water.

4. The method of extending the life expectancy of the high-temperature piping according to claim 1, wherein a heat dissipating member is installed on the outer surface of the high-temperature piping from which the heat insulation material has been removed.

5. The method of extending the life expectancy of the high-temperature piping according to claim 1, wherein the temperature of the outer surface of the high-temperature piping, from which the heat insulation material has been removed, is measured to determine that the cooling capacity is appropriate.

6. The method of extending the life expectancy of the high-temperature piping according to claim 5, wherein, when the cooling capacity is not appropriate, the cooling capacity is changed to be appropriate.

7. A life expectancy extension structure of a high-temperature piping,
   in which a width of an exposed portion of the high temperature piping where a part of a heat insulation material that covers a location having a high creep rupture risk in the high-temperature piping is peeled off is twice or more a distance from an end portion of the exposed portion to a portion where a compressive stress is asymptotical to 0 after a change in stress between a tensile stress and the compressive stress occurring in the high-temperature piping due to the removal of the heat insulation material is made from the tensile stress to the compressive stress, and
   the distance at which the compressive stress after a change in stress is made from the tensile stress to the compressive stress is asymptotical to 0 is based on the following formula (1), $$\beta x = 5 \quad (1)$$

β is expressed by the following formula (2), $$\beta = \sqrt[4]{\frac{3(1-v^2)}{a^2 h^2}} \quad (2)$$

here, x is a distance from the end portion of the exposed portion, v is a Poisson's ratio, and symbol a is an average radius of the piping, and symbol h is a plate thickness of the piping.

8. The life expectancy extension structure of the high-temperature piping according to claim 7, comprising:
   a cooling unit that cools a surface of the exposed portion of the high temperature piping from which the heat insulation material has been removed.

9. The life expectancy extension structure of the high-temperature piping according to claim 8, wherein the cooling unit is an air-cooling unit by air or a water-cooling unit by cooling water.

10. The life expectancy extension structure of the high-temperature piping according to claim 7, wherein a heat dissipating member is installed on the surface of the exposed portion of the high temperature piping from which the heat insulation material has been removed.

* * * * *